(12) United States Patent
Kohayakawa

(10) Patent No.: US 6,309,068 B1
(45) Date of Patent: *Oct. 30, 2001

(54) EYE EXAMINING APPARATUS

(75) Inventor: Yoshimi Kohayakawa, Utsunomiya (JP)

(73) Assignee: Canon Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/127,607

(22) Filed: Jul. 31, 1998

(30) Foreign Application Priority Data

Aug. 5, 1997 (JP) .................................................. 9-223181

(51) Int. Cl.[7] ........................................................ A61B 3/10
(52) U.S. Cl. ............................................................ 351/221
(58) Field of Search ................................... 351/205, 207, 351/208, 211, 212, 221, 223, 246; 600/489, 558; 396/51

(56) References Cited

U.S. PATENT DOCUMENTS

| 3,706,304 | * | 12/1972 | Sisler | 600/489 |
|---|---|---|---|---|
| 3,904,280 | * | 9/1975 | Tate, Jr. | 351/211 |
| 4,874,236 | * | 10/1989 | Abraham | 351/205 |
| 4,923,297 | * | 5/1990 | Arndt | 351/208 |
| 5,561,482 | * | 10/1996 | Miyake | 351/208 |
| 5,737,058 | * | 4/1998 | Umemura et al. | 351/208 |
| 5,795,306 | * | 8/1998 | Shimotani et al. | 600/558 |
| 5,926,655 | * | 7/1999 | Irie et al. | 396/51 |

FOREIGN PATENT DOCUMENTS

| 59-85641 | 5/1984 | (JP) . |
|---|---|---|
| 3-15434 | 1/1991 | (JP) . |
| 5-000126 | 1/1993 | (JP) . |
| 6-007298 | 1/1994 | (JP) . |

* cited by examiner

Primary Examiner—George Manuel
(74) Attorney, Agent, or Firm—Fitzpatrick, Cella, Harper & Scinto

(57) ABSTRACT

This specification discloses an eye examining apparatus having a projection optical system for projecting a light beam onto an eye to be examined, an eye examining optical system for receiving the light of the projection optical system reflected by the eye to be examined and examining the eye to be examined, a face detecting system for detecting the presence of an examinee's face, a driving system for driving the eye examining optical system, and a control system for starting the driving of the driving system on the basis of the result of the detection by the face detecting system, and capable of automatically effecting alignment even if the position of the eye to be examined deviates greatly.

12 Claims, 12 Drawing Sheets

EYE EXAMINING APPARATUS

BACKGROUND OF THE INVENTION

1. Field of the Invention

This invention relates to an eye examining apparatus.

2. Related Background Art (1) In an eye examining apparatus wherein a light beam is projected onto an eye to be examined and the reflected light thereof is received, the alignment of the eye to be examined needs to be performed accurately and therefore, an examiner manually effects the aligning operation. Also, eye examining apparatuses in which delicate alignment is automated are proposed in Japanese Laid-Open Patent Application No. 3-015434 and Japanese Laid-Open Patent Application No. 6-007298.

(2) Further, there are known an eye examining apparatus in which a light beam is projected onto an eye to be examined through a position conjugate with the eye to be examined to thereby effect an eye examination, and an apparatus as disclosed in Japanese Laid-Open Patent Application No. 59-085641 wherein a visual target is presented to both eyes with a variable diopter to thereby effect an eye examination.

(3) In Japanese Laid-Open Patent Application No. 5-000126, there is disclosed an apparatus in which a light dividing member for dividing visible light and infrared light is provided on a visual target unit and a visual target of a wide field of view is presented to thereby effect objective refraction measurement.

(4) In a visual target device, to change diopter without changing the angle of field, there is known a system in which a light beam from a pupil is made into a parallel light beam in front of a visual target and the visual target is moved. Also, as a system in which a portion of an optical system is moved to thereby change diopter, there has been proposed an apparatus in which an afocal converter is moved in the parallel light of a pupil light beam.

(5) Also, there is known a system in which corneal reflected light is received by a light dividing sensor to thereby detect the distance to an eye to be examined.

(6) In Japanese Laid-Open Patent Application No. 5-000126, there are disclosed visual target unit for presenting a visual target to both eyes through a light dividing member and an optical system having a single focus, and a refraction measuring system for effecting refraction measurement through the light dividing member. Also, there is known an eye examining apparatus in which a visual target is presented to one eye and by the changeover of the right and left eyes, an optical system is moved by a predetermined amount in the widthwise direction of the eyes and is three-dimensionally driven for alignment.

(7) Also, there is known a compound machine of an auto-refractometer and an auto-keratometer provided with the refraction measuring system of Japanese Laid-Open Patent Application No. 5-000126, and in addition, a mechanism for moving an optical system including a visual target as a unit for the purpose of alignment.

(i) However, particularly in the apparatus of the example of the prior art described in item (1) above, the examiner manually effects the alignment of the eye to be examined and therefore, accurate alignment cannot be accomplished, and even in an apparatus wherein delicate alignment is automated, there is the problem that at first, the examiner must operate manually.

SUMMARY OF THE INVENTION

It is a first object of the present invention to solve particularly the problem mentioned in item (i) above and to provide an eye examining apparatus in which, even when the position of an eye to be examined deviates greatly, alignment can be performed automatically and an examiner's manual operation is unnecessary.

It is a second object of the present invention to provide an eye examining apparatus which can automatically fix a face irrespective of the shape of the face.

It is a third object of the present invention to provide an eye examining apparatus which can automatically hold an eye to be examined in a proper state.

DESCRIPTION OF THE PREFERRED EMBODIMENTS

Figure 1:
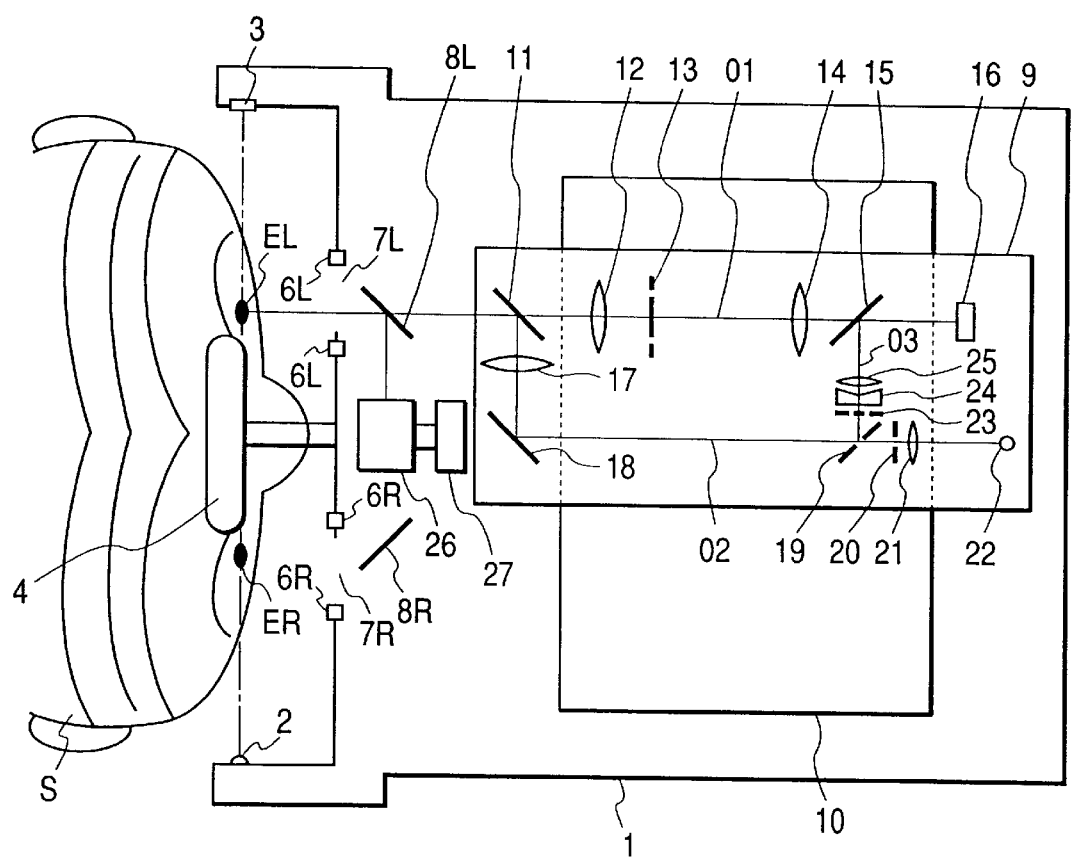
FIG. 1 is a plan view of a first embodiment of the present invention.

The present invention will hereinafter be described in detail with respect to some embodiments thereof shown in the drawings.

Figure 2:
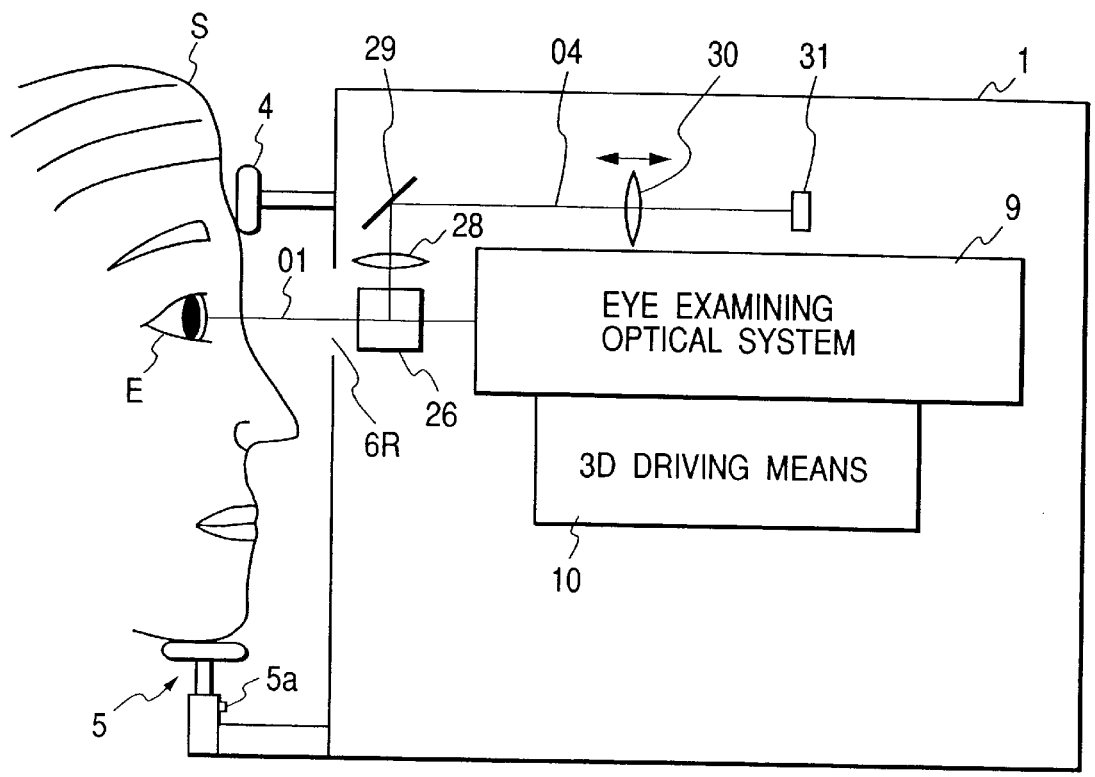
FIG. 2 is a side view of the first embodiment.

FIG. 1 is a plan view of an auto-refractometer according to a first embodiment, and FIG. 2 is a side view thereof. On the examinee side of a housing 1, there are provided face detecting means comprising an LED light source 2 and a photoelectric sensor 3 for detecting the presence of a face, face fixing means comprising a forehead pad 4 and a chin receiving stand 5 adjustable in the longitudinal direction thereof, illuminating light sources 6L, 6R which are infrared LED's for illuminating each of the left eye EL and the right eye ER, and eye examining openings 7L and 7R. Light dividing members 8L and 8R are disposed forwardly of the eye examining openings 7L and 7R, respectively, an eye examining optical system 9 is disposed on an optical path 01 passing through the light dividing member 8L, and the eye examining optical system 9 may be driven by three-dimensional driving means 10 comprising three stepping motors. The forehead pad 4 in the initial state is at an average position, and the chin receiving stand 5 is freely moved with a spring up and down at first, and can be fixed by a stopper 5a. Also, laterally and on top of the face of the examinee S, covers, not shown, are provided so that there may not be created reflected light from corneas by an external light source.

Figure 3:
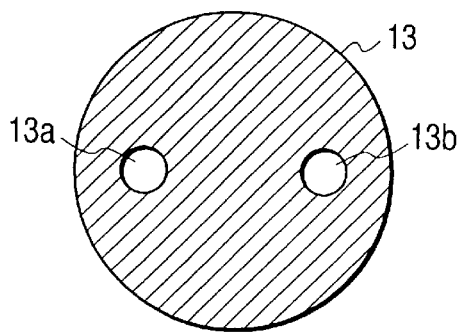
FIG. 3 is a front view of a two-aperture stop.

In the eye examining optical system 9, there are successively arranged on the optical path 01 a light dividing member 11, a lens 12, a two-aperture stop 13 having two apertures 13a and 13b symmetric with respect to the optical path 01 as shown in FIG. 3, a lens 14, a light dividing member 15 and image pickup means 16, and on an optical path 02 in the direction of reflection of the light dividing member 11, there are arranged a lens 17, a mirror 18, an apertured mirror 19, a central opening stop 20, a lens 21 and a light source 22 for refraction measurement. On an optical path 03 in the direction of reflection of the apertured mirror 19, there are arranged a six-aperture stop 23, a separating prism 24 and a lens 25, and this optical path leads to the light dividing member 15. The light dividing members 11 and 15 have the function of transmitting the wavelength lights of the illuminating light sources 6L and 6R therethrough and reflecting the wavelength light of the light source 22 for refraction measurement.

A changeover mirror 26 is disposed substantially centrally of the direction of reflection of the light dividing members 8L and 8R, and the changeover mirror 26 may be driven by a solenoid 27. On an optical path 04 in the direction of reflection upward from the changeover mirror 26, there are arranged a lens 28, a mirror 29, a focusing lens 30 and a visual target 31, and these members 28 to 31 are contained in the housing 1.

In the above-described construction, when a main power source switch, not shown, is closed during measurement, the face detecting means for the examinee S becomes capable of detecting. The face detecting means is such that when the examinee's face is absent, the light beam of the LED light source 2 is not hampered but enters the photoelectric sensor 3 and a predetermined quantity of light is detected. When the examinee's face comes to its position shown in FIG. 1, this light beam is intercepted and by a decrease in the quantity of light thereof, the presence of the face is judged. When the face is detected, the illuminating light source 6L and the light source of the visual target 31 are turned on, and the image pickup means 16 becomes operative.

The examinee applies his forehead to the forehead pad 4 which in the initial state is at an average position, and places his chin on the chin receiving stand 5 and looks into the eye examining openings 7L and 7R. When the left eye EL is to be detected as shown in FIG. 1, the illuminating light source 6L is turned on. The changeover mirror 26 faces the light dividing member 8L, and the light beam from the visual target 31 passes the focusing lens 30, the mirror 29, the lens 28, the changeover mirror 26 and the light dividing member 8L and the visual target 31 is presented to the eye EL to be examined. Also, the image of the anterior eye part illuminated by the illuminating light source 6L passes the optical path 01, and is picked up by the image pickup means 16 via the light dividing members 8L, 11, the lens 12, the two-aperture stop 13, the lens 14 and the light dividing member 15.

Figure 4:
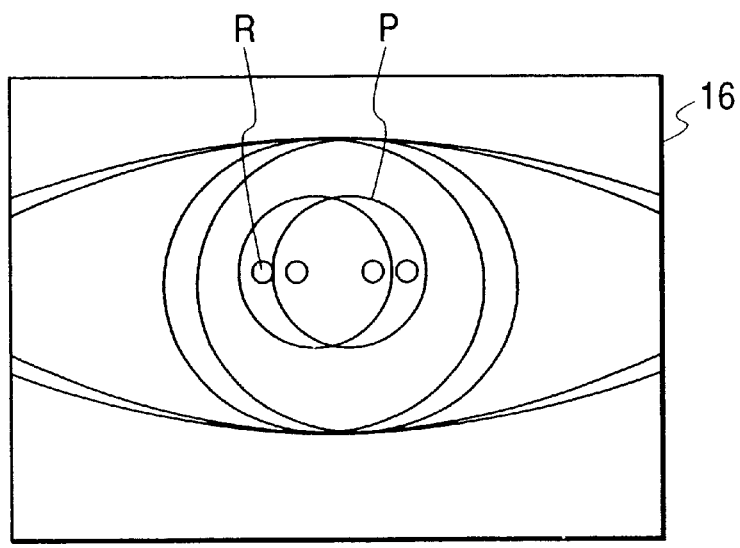
FIG. 4 is an illustration of the image of an anterior eye part.

FIG. 4 shows the image of the anterior eye part picked up by the image pickup means 16, and represents a pupil image P and a corneal reflected image R by the illuminating light source 6L. When the eye E to be examined is not at a predetermined distance, the image becomes double, and this image signal is calculated by calculating means and the eye E to be examined is recognized. When the position of the eye E to be examined is to be recognized by the use of the corneal reflected image R or the pupil image P, the corneal reflected image R is higher by one figure or greater in the level of quantity of light than the other portions of the image field and is therefore easy to grasp, and owing to the presence of the two-aperture stop 13, blur is little even if the distance deviates, and a high level of quantity of light is kept and recognition is easy. Further, the pupil image P is displayed darkly and is low in the level of quantity of light as compared with the other portions of the image field and can therefore be recognized easily. During the recognition by calculation, besides the levels of quantity of light of the corneal reflected image R and the pupil image P, the sizes and circular shapes thereof are also taken into account.

The image signal of the image pickup means 16 is analyzed by a computer, and when the eye E to be examined is recognized in the image field of the image pickup means 16, the stopper 5a is operated and the vertical position of the chin receiving stand 5 is fixed. Thereby, the height of the chin receiving stand 5 is automatically adjusted.

Next, the driving means 10 of the eye examining optical system 9 is operated and on the basis of the position information of the eye to be examined from the image pickup means 16, distance adjustment is performed so that double images of the eye to be examined may overlap each other, and further, axial alignment is performed so that the pupil image P may come to a predetermined position on the image field. When the distance cannot be completely adjusted by the driving means 10, the forehead pad 4 is driven back and forth on the basis of the signal of the image pickup means 16 to thereby adjust the distance.

When alignment has been done, the illuminating light source 6L is turned off and the light source 22 for refraction measurement is turned on, and the light beam of the light source 22 for refraction measurement passes through the optical path 02 and is projected onto the left eye EL to be examined via the central opening stop 20, the apertured mirror 19, the mirror 18, the lens 17 and the light dividing members 11 and 8L. The reflected light thereof from the fundus of the eye returns along the optical paths 01 and 02 and passes through the optical path 03, and is received as six spot lights by the image pickup means 16 via the six-aperture stop 23, the separating prism 24, the lens 25 and the light dividing member 15. From this signal, the position of the lights are calculated by a computer and the refraction value is calculated, and the result is displayed on a printer, not shown.

In order to measure the right eye ER, the eye examining optical system 9 is driven by the three-dimensional driving means 10 and is aligned with the eye ER to be examined. The changeover mirror 26 is changed over by the solenoid 27 and a visual target 31 is projected onto the right eye ER through the light dividing member 8R. Thereafter, as in the case of the above-described left eye EL, axial adjustment and alignment are performed, after which refraction measurement is carried out.

Figure 5:
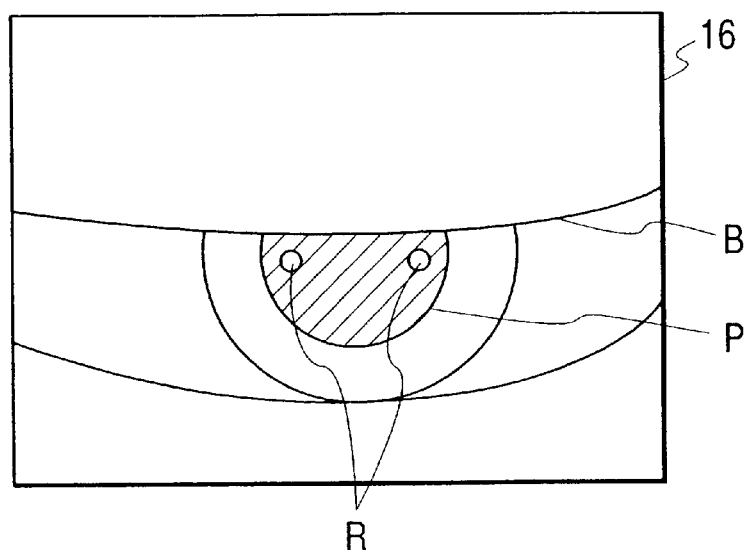
FIG. 5 is an illustration of the image of the anterior eye part with the eye lid lowered.

FIG. 5 shows an image on the image pickup means 16 when the eyelid lowers so that it covers part of the pupil of the eye to be examined. The shape in which the upper portion of the pupil image P of circular shape has broken is calculated and it is recognized that the eyelid image B has lowered. Also, it can also be recognized that the corneal reflected image R is not symmetrical in the vertical direction of the pupil image P, and if the lowered state of the eyelid image B is of such a degree that it hampers a measuring light beam, a warning display is performed by a composite voice to thereby call upon the examinee S to further open his/her eyes.

Figure 6:
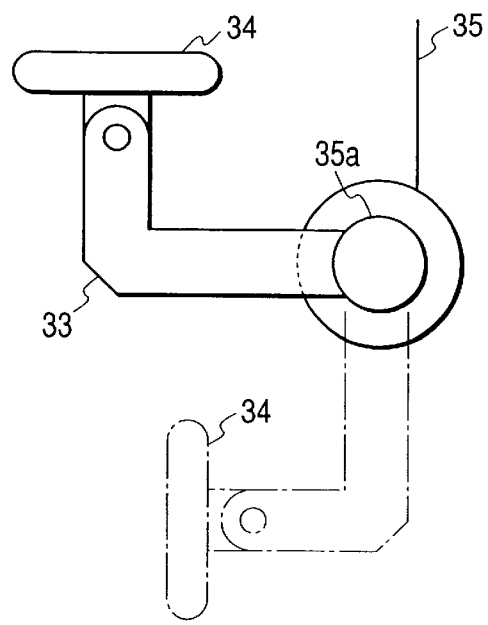
FIG. 6 is a side view of another embodiment of a chin receiving stand.

FIG. 6 shows another embodiment of the chin receiving stand. A chin receiving stand 34 is fixed to an arm 33, which in turn is mounted on the shaft 35a of an ultrasonic motor 35, and the chin receiving stand 34 is arranged to be rotated about the shaft 35a through the arm 33.

The chin receiving stand 34 in its initial state is lowered to a position indicated by dotted line, and when the eye E to be examined is recognized by the signal of the image pickup means 16, the ultrasonic motor 35 is rotated and the chin receiving stand 34 comes to its solid-line position and reaches the examinee's chin, and the supply of electric power to the ultrasonic motor 35 is cut off, and the arm 33 and the chin receiving stand 34 are fixed at that position.

Figure 7:
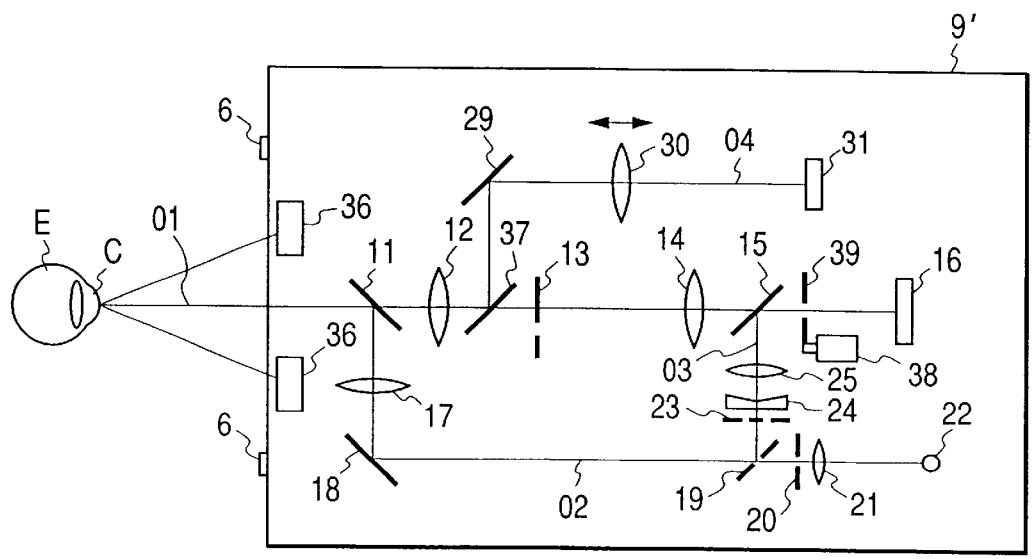
FIG. 7 is a side view of an optical system according to a second embodiment.

Referring to FIG. 7 which is a side view of the optical system 9' of a compound machine of an auto-refractometer and an auto-keratometer according to a second embodiment, the same members as those in the first embodiment are designated by the same reference numerals as those in the first embodiment, and the same constituent portions are not shown. A light source 6 for illuminating the anterior eye part and a ring light source 36 for projecting a light beam onto the cornea C of the eye E to be examined are disposed on the front face of the optical system 9', and on an optical path 01 in the optical system 9', there are successively arranged a light dividing member 11, a lens 12, a light dividing member 37 reflecting visible light, a two-aperture stop 13, a lens 14, a light dividing member 15, a stop 39 connected to a solenoid 38 which is inserted only during the measurement of the cornea, and an image pickup element 16.

The two-aperture stop 13 is comprised of a dichroic mirror, and the wavelength light of the ring light source 36 is completely transmitted therethrough, and the two-aperture stop becomes effective at the wavelength of light of the illuminating light source 6. In the present embodiment, a visual target optical system is also contained in the optical system 9', and a mirror 29, a focusing lens 30 and a visual target 31 are arranged on an optical path 04 in the direction of reflection of the light dividing member 37.

By the above-described construction, the visual target light beam from the visual target 31 is projected onto the eye E to be examined via the focusing lens 30, the mirror 29, the light dividing member 37, the lens 12 and the light dividing member 11. Also, the ring light source 36 projects a ring light beam onto the cornea C of the eye E to be examined, and the corneal reflected image R thereof passes along the optical path 01 and is received by image pickup means 16 through the light dividing member 11, the lens 12, the light dividing member 37, the two-aperture stop 13, the lens 14, the light dividing member 15 and the stop 39, and the shape of the ring image is recognized by calculation and the measurement of the shape of the cornea is performed.

The alignment of the eye E to be examined during the measurement of the cornea is performed with the corneal reflected image R by the illuminating light source 6 or the ring light source 36 calculated and the driving means 10 driven. That is, distance adjustment is performed so that double corneal reflected images R may overlap each other, and alignment is performed so that the overlapping corneal reflected images R on both sides may come to a predetermined image field position. During the alignment, the ring light source 36 is turned on, and whether the eyelid image B is lowered as shown in FIG. 5 is calculated and determined by whether the upper portion of the ring image has broken, and if the eyelid image is lowered, a composite voice is uttered to thereby effect indication for instructing the examinee to raise his or her eyelids. The measurement of refractive power performed through the optical paths 02 and 03 is similar to that in the first embodiment and therefore need not be described.

Figure 8:
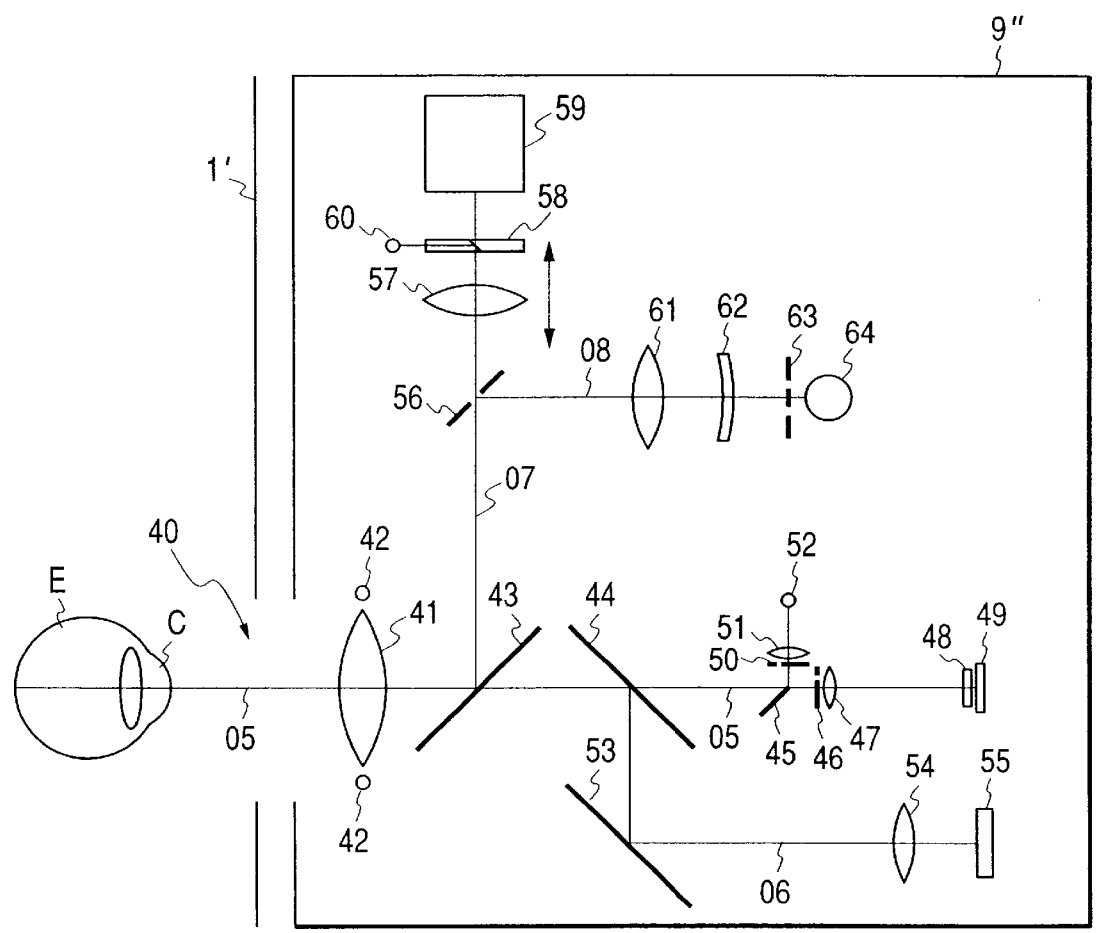
FIG. 8 is a side view of an optical system according to a third embodiment.

Referring to FIG. 8 which is a side view of a retinal camera capable of effecting automatic photographing according to a third embodiment, face fixing means comprising a forehead pad 4 and a chin receiving stand 5 and driving means 10 for driving an optical system 9'' are similar to those in the first embodiment and therefore are not shown. Eye examining openings 40 for the left and right eyes EL and ER are provided on the examinee side of a housing 1', and window glass, not shown, inclined with respect to an optical path 05 to avoid the reflection of a light beam is attached to each of the eye examining openings 40.

An objective lens 41 is provided on the optical path 05 of an optical system for measuring the refraction of the eye E to be examined, and anterior eye part illuminating light sources 42 emitting infrared light are disposed around the objective lens 41, and further on the optical path 05 rearward of the objective lens 41, there are successively arranged a light dividing member 43 transmitting infrared light therethrough and reflecting visible light, a light dividing member 44, a half mirror 45 located on one side of the optical path 05, a small aperture stop 46 conjugate with the pupil, a lens 47, a cylindrical lens 48 and a one-dimensional CCD 49. In the direction of incidence of the half mirror 45, there are disposed a small aperture stop 50 conjugate with the pupil, a lens 51 and a light source 52 for measuring the refraction of the infrared light wavelength differing from the anterior eye part illuminating light sources 42, and on the optical path 06 of an anterior eye part image pickup optical system in the direction of reflection of the light dividing member 44 for spectrally dividing the illuminating light sources 42 and a refraction measuring light source 52, there are arranged a mirror 53, a lens 54 and image pickup means 55.

Also, on the optical path 07 of an eye fundus photographing optical system in the direction of reflection of the light dividing member 43, there are successively arranged an apertured mirror 56 conjugate with the anterior eye part, a focusing lens 57, a light dividing member 58 reflecting part of visible light, and image pickup means 59, and in the direction of incidence of the light dividing member 58, there are two light sources 60 for fixation discretely by the left and right eyes. Also, on the optical path 08 of an eye fundus illuminating optical system in the direction of incidence of the apertured mirror 56, there are arranged a lens 61, a concave mirror 62 reflecting part of visible light, a ring slit 63 conjugate with the pupil and light source 64 of the strobe.

In the above-described construction, when the examinee S looks into the eye examining openings 40, the above-mentioned face detecting means is operated and the light source 60 for fixation corresponding to the left or right eye to be examined is turned on, and an alignment system becomes operative. The light beam from the light source 60 for fixation is projected onto the eye E to be examined through the light dividing member 58, the lens 57, the apertured mirror 56, the light dividing member 43 and the objective lens 41. This fixation light is projected from the photo-taking optical path and therefore is not seen unless the axis is adjusted to some degree. When the examinee looks into the openings, his anterior eye part image is seen by virtue of the reflection of the concave mirror 62 and therefore, if rough axial adjustment is done, the fixation lamp 60 will be seen.

Also, when the eye E to be examined lies at a predetermined position, the illuminating light source 42 illuminates the anterior eye part of the eye E to be examined, and the image of the anterior eye part is formed on the image pickup means 55 through the objective lens 41, the light dividing members 43, 44, the mirror 53 and the lens 54. At first, the distance is not adjusted and therefore the image is blurred and thus, the position of the eye E to be examined cannot be recognized by calculation, but yet the reflected light from the face by the light beam of the illuminating light source 42 is received. When there is a predetermined level of light reception, it is judged that the examinee's face is present, and the focusing operation is started by the use of the driving means 10. The optical system 9" is moved back and forth in the fashion of trial and error, and is first driven so that the high frequency component of an image video signal may become much, and is driven back and forth so that the pupil image, when recognized, may be in focus. Thereafter, alignment is performed so that the pupil may come to a predetermined image field position, and alignment is three-dimensionally done. The configuration and size of the pupil image are recognized, and when the size of the pupil image is deficient, the indication for instruction of phototaking being impossible is performed, and when the eyelids have lowered, indication for instructing the examinee to open his eyes by voice uttering means is performed.

The light beam of the refraction measuring light source 52 passes through the lens 51, the small aperture stop 50, the half mirror 45, the light dividing members 44, 43 and the objective lens 41, and projects a spot light from one side of the pupil of the eye E to be examined onto the fundus of the eye. The reflected light thereof returns along the optical path 05 from the other side of the pupil, and is received by the one-dimensional CCD 49 through the small aperture stop 46, the lens 47 and the cylindrical lens 48. The refractive value is calculated on the basis of the light position on this one-dimensional CCD 49. The focusing lens 57 of the image pickup optical system is driven by the signal thereof and the image of the fundus of the eye is focused, and the strobe light source 64 is caused to emit light and thereby effect photo-taking. The light beam from the strobe light source 64 illuminates the fundus of the eye to be examined through the ring slit 63, the concave mirror 62, the lens 61 and the apertured mirror 56, and the image of the fundus of the eye is recorded by the image pickup means 59 and is immediately outputted to a video printer.

Figure 9:
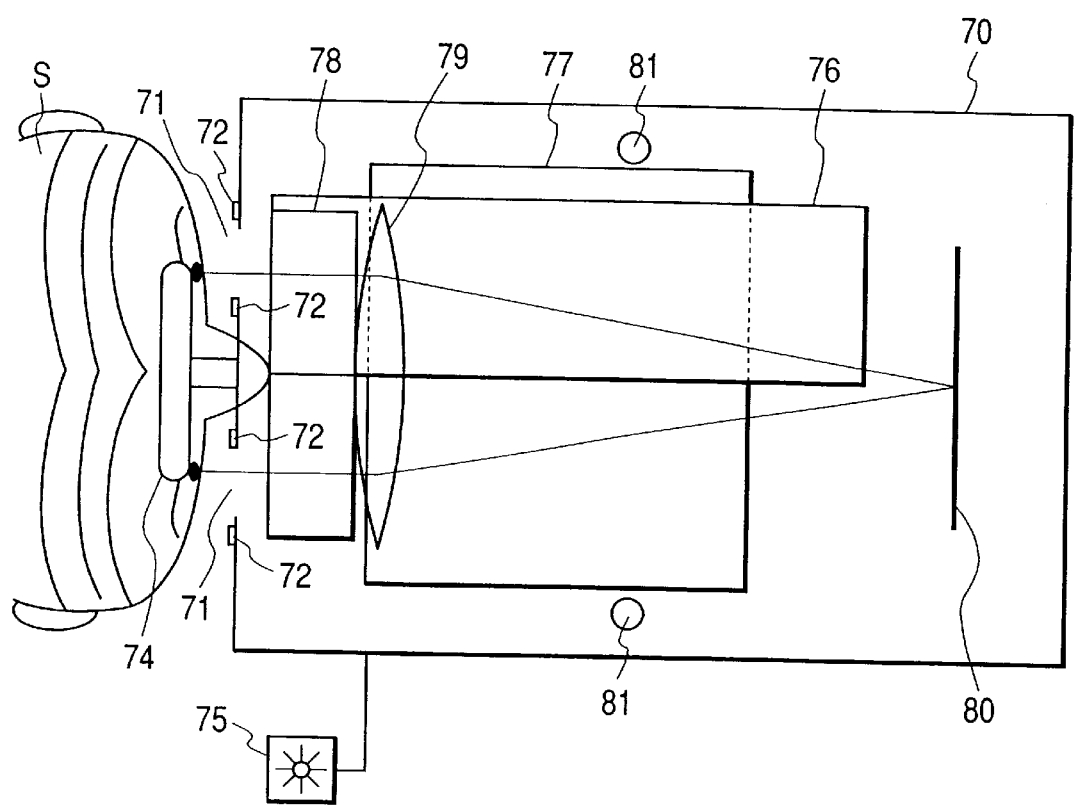
FIG. 9 is a plan view of a fourth embodiment.
Figure 10:
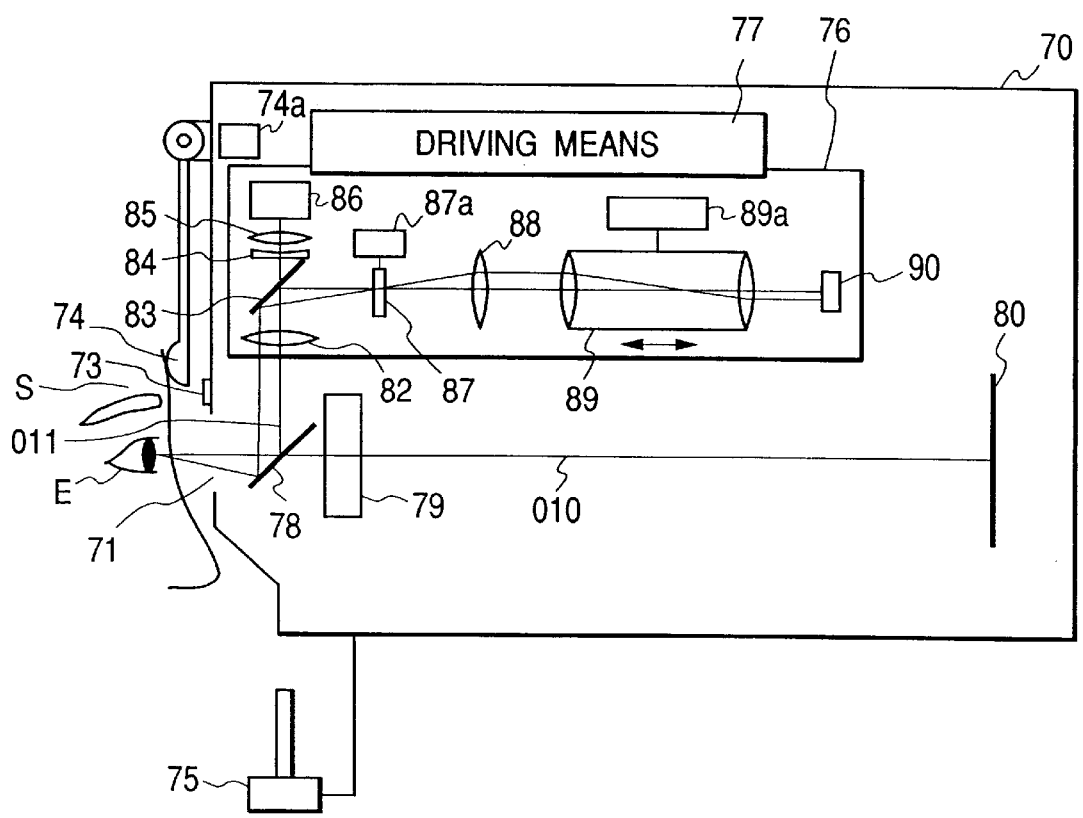
FIG. 10 is a side view of the fourth embodiment.

FIG. 9 is a plan view of an eye examining apparatus for subjective refraction measurement or eyesight measurement according to a fourth embodiment, and FIG. 10 is a side view thereof. Two left and right eye examining openings 71 are provided on the examinee side of a housing 70, and anterior eye part illuminating light sources 72 of infrared light are disposed on the opposite sides of each of the openings 71. Face detecting means 73 comprising an infrared LED and a light receiving element is provided in the upper portion of each opening 71 so as to receive the reflected light from the examinee's face and detect the face by the signal level thereof. Further, there are provided a forehead pad 74 adjustable back and forth by driving means 74a and responding means 75 operable by the examinee.

In inside of the housing 70, there are disposed an eye examining optical system 76, driving means 77 for three-dimensionally driving this eye examining optical system 76 by three stepping motors to align the eye examining optical system 76, and a binocular visual target optical system. On the optical path 010 of the binocular visual target optical system forward of the eye E to be examined, there are successively arranged a light dividing member 78, a lens 79 wider than the distance of both eyes E to be examined, and a binocular visual target 80, and the binocular visual target 80 is disposed near the focus of the lens 79 so as to become apparently far, and visual target illuminating light sources 81 are provided forwardly of the binocular visual target 80. A concave mirror and a half mirror may be used instead of the lens 79.

Figure 11:
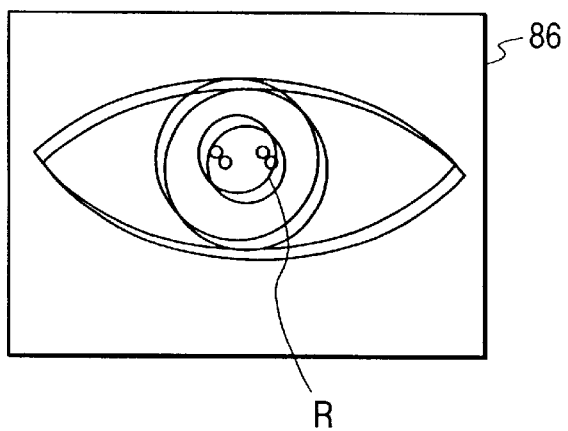
FIG. 11 is an illustration of the image of the anterior eye part.
Figure 12A:
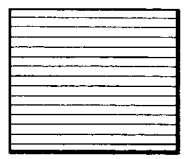
FIGS. 12A, 12B and 12C are illustrations of visual targets.
Figure 12B:
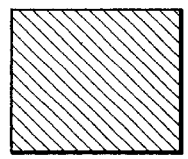
Figure 12C:
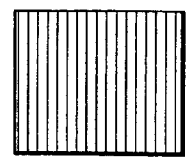

On the optical path 011 of the eye examining optical system 76 in the direction of reflection of the light dividing member 78, there are successively arranged a lens 82, a light dividing member 83, wedge prisms 84 for vertically separating the images of the eye to be examined as shown in FIG. 11, a lens 85 and anterior eye part image pickup means 86. In the direction of incidence of the light dividing member 83, there are arranged a cross cylinder lens 87 for correcting astigmatism driven by driving means 87a and disposed at a position conjugate with the pupil, a lens 88, a variable diopter lens 89 driven by driving means 89a, and a visual target 90 comprising liquid crystal image display means. Striped patterns in three directions as shown in FIGS. 12A, 12B and 12C which are stored in a contained memory, not shown, are adapted to be displayed in accordance with a program on the visual target 90 of which the visual angle is 5 to 10 degrees.

By the above-described construction, the binocular visual target 80 illuminated by the visual target illuminating light sources 81 and the visual target 90 of the eye examining optical system 76 are overlappingly presented to the examinee S through the light dividing member 78. The visual target 80 is presented to the examinee's both eyes through the lens 79 and the light dividing member 78, and the visual target 90 is presented to the eye E to be examined through the variable diopter lens 89, the lens 88, the cross cylinder lens 87, the light dividing member 83, the lens 82 and the light dividing member 78.

Figure 13:
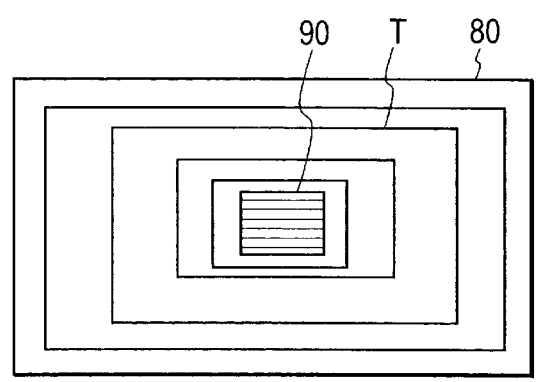
FIG. 13 is a front view of the field of view of the visual target.

FIG. 13 shows the visual target field of view in a state in which the visual target 80 and the visual target 90 are overlappingly seen, and a frame pattern T is depicted around the visual target 80, and at the central portion, there is not the pattern T but the visual target 90 is overlappingly seen. The visual angle is 20° to 40° and has the function of keeping the eye E to be examined in a far seeing state. The examinee S brings down an operating rod in the direction of the presented striped pattern and responds by the responding means 75, and inputs the response to the control calculation means, not shown, of the apparatus.

When the switch from an external power source is on, only the face detecting means 73 is kept in its operative state. When the eye E to be examined is brought close to the eye examining opening 71, the face detecting means 73 detects a predetermined or greater quantity of light by the reflection of the face, and the light sources for illuminating the visual targets 80 and 90 are turned on. Whether the forehead contacts the forehead pad 74 is detected by a microswitch mounted on the forehead pad 74, and if it does not, a voice for calling the examinee's attention is uttered from a voice generating device. The anterior eye part illuminated by the illuminating light source 72 is vertically separately imaged by the image pickup means 86, as shown in FIG. 11. From the direction and degree of the deviation of this double image, the distance and the direction of the deviation can be known and therefore, this image is calculated by calculating means and is analyzed. Particularly, the corneal reflected image R which is high in signal intensity is extracted and the distance is calculated from its relative position in the lateral direction, and the axial alignment is calculated from its position in the image field, and the result is fed back to the driving means 77 and alignment driving is performed.

The distance from the forehead to the eyes differs from person to person and sometimes the image on the image pickup means 86 is blurred and the corneal reflected image R cannot be recognized, but when the signal level of the image is within a predetermined range, it is Judged that there is the face, and the driving means 74a is driven to move the forehead pad 74 back and forth, and a position where the image pickup means 86 can recognize the eye is looked for. When the positioning has done to some degree, the presentation of the visual target 90 is started. The examinee is instructed in a voice, when he or she can the stripe to respond bringing down the operating not in the direction of the stripe. At first, start is performed from a striped pattern of a pitch corresponding to the eyesight of 0.3, and the variable diopter lens 89 is driven by the driving means 89a and the visual target diopter is moved from afar to near.

Figure 14:
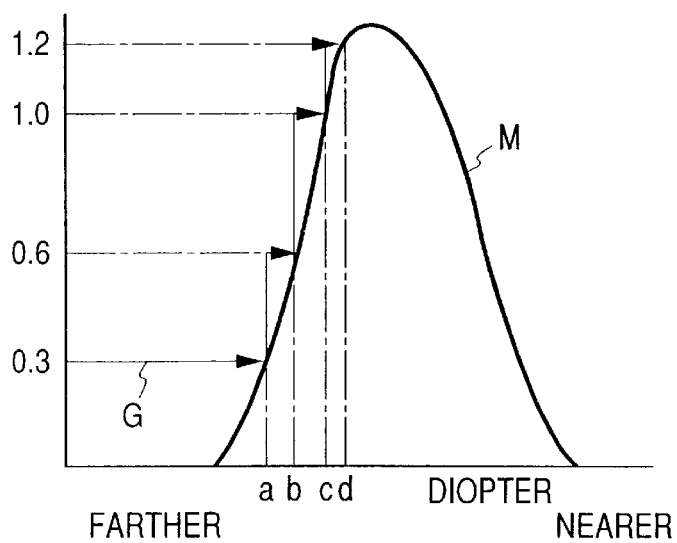
FIG. 14 is a graph of eyesight measurement.

FIG. 14 is a graph showing the procedure of eyesight measurement, and the axis of ordinates represents the pitch of the striped pattern representative of eyesight, and the axis of abscissas represents the visual target diopter. A curve M indicates the relation between the eyesight and the visual target diopter when the diopter of the eye is being fixed, and a line G represents the presented visual target. When the accomodation of the eye works, the largest slope of M moves to near. The examinee S can see at the diopter of a intersecting with the curve M and then response. When there is a response, a response recognizing sound is uttered and the striped pattern is once turned off, and then a striped pattern of the eyesight 0.6 is presented from the diopter a and the visual target 90 is moved to near. If there is a response for diopter b, start is now performed from the diopter b at eyesight 1.0.

In this manner, diopter d corresponding to the position of the shoulder of the far side slope of M is found. This represents the degree of refraction in a meridian direction perpendicular to the striped pattern used, and the degrees of refraction in respective directions are successively found by the use of the striped patterns in the two other directions. However, from the second direction, start can be performed from eyesight 1.0, and from the degrees of refraction in those three meridian directions, assuming that the variation in the meridian direction is sinusoidal, a refractive value comprising a degree of spherical refractive value, a degree of astigmatism and an astigmatic angle is calculated.

When astigmatism is strong, the eyesight by a striped pattern is not obtained and therefore, when the measured eyesight is 0.5 or less, it is judged that astigmatism is strong, and the degree of refraction of two vertical and horizontal meridians is first measured, and on the basis of this, the cross cylinder lens 87 is driven by the driving means 87a, and vertical and horizontal rough astigmatism correction is performed, and then the degrees of refraction in three directions are measured to thereby find the refractive value. To measure eyesight, the diopter and astigmatism of the visual target 90 are set according to the measured dioper and astigmatism, and they are presented, gradually roughening from a fine striped pattern till responding when the striped pattern is seen. There are carried out by the striped visual targets in three directions, and the eyesight is calculated from the pitch of those striped patterns. When the difference among the three directions is great, it is possible that astigmatism is not sufficiently corrected and therefore, in that astigmatism corrected state, the degrees of refraction in the three directions are again measured and confirmed. If the diopter of the spectacles the examinee is wearing is measured by a lens meter and this is set as the initial value in the visual target optical system, the measurement time can be shortened.

Figure 15:
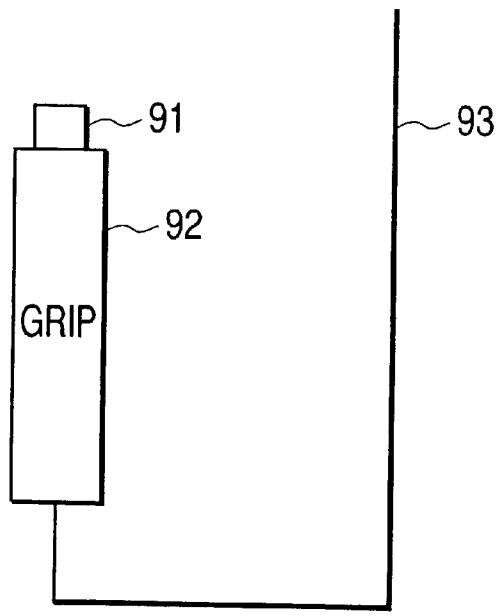
FIG. 15 is a side view of responding means.

FIG. 15 shows another embodiment of the responding means, and the output of a grip 92 having a switch 91 at the head thereof is connected to calculation controlling means, not shown, by a signal line 93.

The grip 92 is gripped and the switch 91 is pushed by the thumb during response, and a response signal is sent to the calculation controlling means by the signal line 93. When the striped pattern is seen irrespective of the direction of the striped pattern, voice instructions can be given so as to depress the switch 91 and therefore, direction inputting is simpler.

Figure 16:
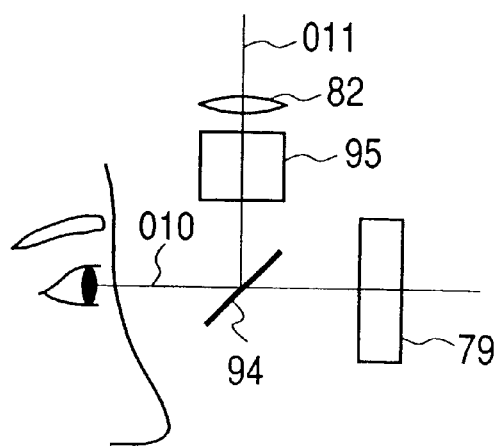
FIG. 16 is a side view of the essential portions of a fifth embodiment.

FIG. 16 is a side view of the essential portions of a fifth embodiment having the objective refraction measuring function, and the other portions are similar to those of the fourth embodiment and therefore are not shown. A light dividing member 94 corresponding to the light dividing member 78 shown in FIG. 10 has a width of only one eye optical path and is adapted to be driven with other optical system by the driving means 77. A visual target optical system similar to that of FIG. 10 is disposed in the direction of transmission of the light dividing member 94, a dichroic mirror 95 reflecting an objective refraction measuring light beam is disposed on an optical path 011 in the direction of reflection of the light dividing member 94, and an eye examining optical system 76 for effecting objective refraction measurement as in FIG. 10 is disposed in the direction of reflection of the dichroic mirror 95.

By the above-described construction, the eye examining optical system 76 is integrally driven to thereby effect alignment and the changeover of the left and right eyes. Objective refraction measurement is first performed and the measured value is used as the initial value of the visual target optical system during subjective measurement. That is, the degree of astigmatism is set to that value and diopter is started from a little farther side than that. During objective measurement too, the visual target 90 is used, and the measurement is performed with the image of a distant view displayed.

Figure 17:
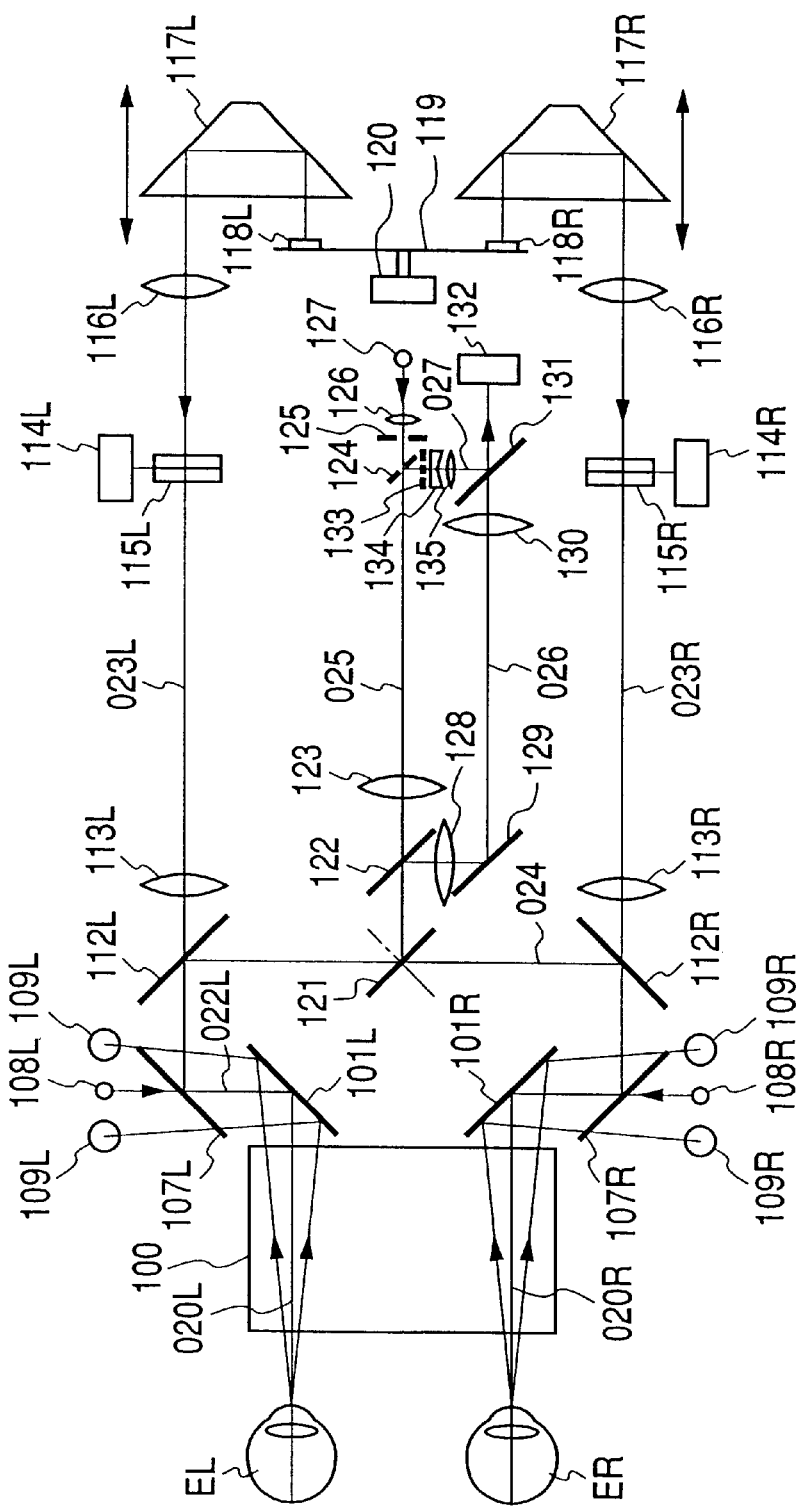
FIG. 17 is a plan view of an optical system according to a sixth embodiment.
Figure 18:
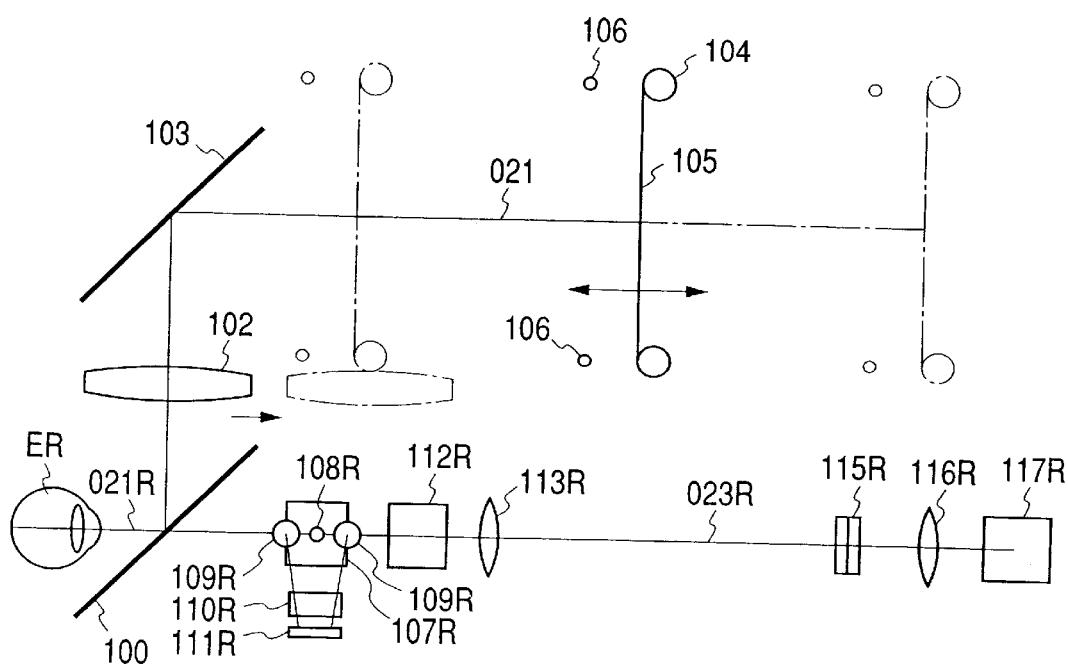
FIG. 18 is a side view of the optical system of FIG. 17.

FIG. 17 is a plan view of the optical system of a subjective-objective refraction measuring apparatus according to a sixth embodiment, and FIG. 18 is a side view thereof. In front of the eyes EL and ER to be examined, there is disposed a light dividing member 100 comprising a half mirror of which the lateral size is larger than the width of the eyes, and on the optical paths 020L and 020R of the left and right eyes EL and ER in the direction of transmission of this light dividing member 100, there are disposed reflecting mirrors 101L and 101R of variable angles.

On an optical path 021 in the direction of incidence above the light dividing member 100, there is provided the movable lens 102 of a far seeing visual target optical system of which the lateral diameter is larger than the width of the eyes, and a mirror 103 and a visual target 105 wound on a roll 104 are successively arranged rearwardly of this movable lens 102. During near distance eye examination, the movable lens 102 is adapted to be retracted from the optical path 021. The visual target 105 comprises various kinds of peripheral visual targets depicted on a thin member such as cloth wound on the roll 104, and the central portion C thereof is a circular blank portion which made low in reflectance. Also, an illuminating light source 106 is disposed forwardly of the visual target 105, which is movable back and forth on the optical path 021 with the illuminating light source 106, and the visual angle of which is of the order of 20° in the vertical direction and is of the order of 30° in the horizontal direction.

On optical paths 022L and 022R in the directions of reflection of the reflecting mirrors 101L and 101R, there are disposed dichroic mirrors 107L and 107R and distance detecting light sources 108L and 108R emitting infrared light, and a set of two concave mirrors 109L and 109R are disposed on the opposite sides of the light sources 108L and 108R. In the directions in which each two concave mirrors 109L and 109R reflect, there are disposed cylindrical lenses 110L and 110R and line array sensors 111L and 111R (110L and 111L being not shown).

On the optical paths 023L and 023R of the visual target optical system in the directions of reflection of the dichroic mirrors 107L and 107R, there are successively arranged dichroic mirrors 112L and 112R, lenses 113L and 113R, cross cylinder lenses 115L and 115R for correction driven by rotatively driving means 114L and 114R and conjugate with the pupil, lenses 116L and 116R, prisms 117L and 117R, and a visual target disc 119 having various second visual targets 118L and 118R on the circumference thereof, and the visual target disc 119 is adapted to be rotated by a stepping motor 120.

The visual angle of the visual targets 118L and 118R is of the order of 3 to 5 degrees, and distant view continuing the central portion A of the visual target 105 is depicted, and this central visual target is adapted to be presented with its diopter changed in conformity with the degrees of refraction of the eyes EL and ER to be examined. Also, the diopter of the visual targets 118L and 118R can be changed with the prisms 117L and 117R moved in the directions of the optical path 023L and 023R in conformity with the degrees of refraction of the left and right eyes EL and ER.

Optical paths 024 in the directions of reflection of the dichroic mirrors 112L and 112R are the same, and a changeover mirror 121 is disposed substantially centrally of this optical path 024. On the optical path 025 of refraction measuring optical system in the direction of reflection of the changeover mirror 121, there are successively arranged a dichroic mirror 122, a lens 123, an apertured mirror 124, a stop 125, a lens 126 and a position detecting and refraction measuring light source 127 emitting infrared light of a wavelength differing from that of the light sources 108L and 108R.

On an optical path 026 in the direction of reflection of the dichroic mirror 122, there are arranged a lens 128, a mirror 129, a lens 130, a dichroic mirror 131 reflecting the wavelength light of the light source 127, and image pickup means 132 conjugate with the fundus of an emmetropia and used for the observation of the anterior eye part for objective refraction measurement and for alignment. On an optical path 027 in the direction of reflection of the apertured mirror 124, there are arranged a pupil periphery six-aperture stop 133 conjugate with the pupil, a separating prism 134 and a lens 135, and this optical path leads to the dichroic mirror 131.

By the above-described construction, the examinee's face is fixed to the face receiving stand, and the examiner drives an optical system placed on a slidable stand, not shown, and effects alignment relative to the eye E to be examined while watching a monitor for alignment. The examinee S sees the peripheral visual target 105 with his two eyes EL and ER through the light dividing member 100, the movable lens 102 and the mirror 103. The visual target 105 is adjusted to the vicinity of the focus of the movable lens 102 during far seeing eye examination, and the light beam from the visual target 105 enters the both eyes EL and ER as parallel light and therefore, there is a far seeing feeling and the accomodation is loosened.

Figure 19:
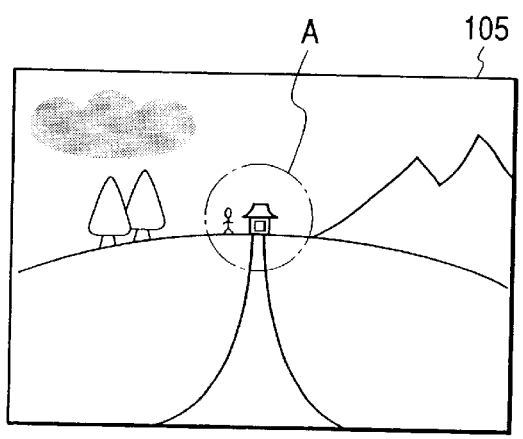
FIG. 19 is an illustration of the field of view of a visual target.

The visual target disc 119 is rotated by the stepping motor 120 to thereby interchange the visual targets 118L and 118R, and the visual targets 118L and 118R which are at symmetrical positions are projected onto the left and right eyes EL and ER with variable diopters through the prisms 117L and 117R, the lenses 116L and 116R, the cross cylinder lenses 115L and 115R, the lenses 113L and 113R, the dichroic mirrors 112L, 112R, 107L and 107R, the reflecting mirrors 101L and 101R and the light dividing member 100. Thereby, the visual targets 118L and 118R are overlappingly presented to the visual target 105 through the light dividing member 100, and a distant view as shown in FIG. 19 is seen to the examinee S.

The peripheral visual target 105 is fixed afar and therefore becomes blurred to eyes which are abnormal in refraction, but it is in the periphery of the field of view and therefore does not become an accomodation stimulus, and even for a blurred peripheral image, the relative positional relation between the image of the funduses of the left and right eyes can be judged and the recognition of the far distance is possible. Accordingly, when the light beam from the visual target 105 is projected in parallelism to the optical paths 020L and 020R of the left and right eyes EL and ER, a far seeing feeling is given to the examinee S. During far seeing eye examination, the optical paths 020L and 020R forward of the eyes EL and ER to be examined are parallel to each other.

In the case of astigmatism, correction is performed with the cross cylinder lenses 115L and 115R rotated by the driving means 114L and 114R, and since the front side focus positions of the lenses 116L and 116R are conjugate with the pupil, the space between the lenses 116L and 116R and the space between the visual targets 118L and 118R are parallel to the light beam from the pupil, and even if the diopter is changed by the prisms 117L and 117R, the visual angles of the visual targets 118L and 118R will not change.

The eyes EL and ER to be examined are illuminated by an anterior eye part illuminating light source, not shown, of which the wavelength differs from that of the infrared LED light source 127, and the image of the anterior eye part is reflected by the dichroic mirror 122 reflecting the wavelength light of that light source, is transmitted through the dichroic mirror 131, is picked up by the image pickup means 132 and is observed on a monitor, not shown. Since the lens 128 is not large, the image of the anterior eye part on the monitor is great in depth of focus and whether the eyelashes hang on the pupil or not can be seen, but it is difficult to adjust the distance by the degree of blur and therefore, distance detecting means is provided and the result of the detection thereby is displayed in the form of a figure on the monitor with the image of the anterior eye part. Alignment is adjusted by the image of the anterior eye part and the distance is adjusted by the figure display by the distance detecting means.

Figure 20:
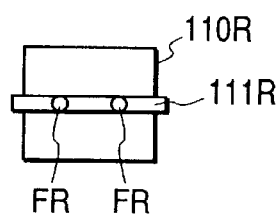
FIG. 20 is a front view of an alignment detecting sensor.

Also, the light beams from the light sources 108L and 108R of an infrared wavelength differing from that of the infrared LED light source 127 illuminate the anterior eye part via the dichroic mirrors 107L and 107R, the mirrors 101L and 101R and the light dividing member 100. The corneal reflected lights thereof are received as two light beams FL and FR from two directions by the line array sensors 111L and 111R via the concave mirrors 109L and 109R and cylindrical lenses 110L and 110R, as shown in FIG. 20. The concave mirrors 109L and 109R image the anterior eye part on the line array sensors 111L and 111R, and the cylindrical lenses 110L and 110R image the concave mirrors 109L and 109R on the line array sensors 111L and 111R.

Even if the corneal reflected lights deviate from the optical paths 020L and 020R, they can be received by the line array sensors 111L and 111R owing to the action of the cylindrical lenses 110L and 110R. That is, when alignment is adjusted by the pupil, the corneal reflected lights may not always come to the center of the pupil, but even in such a case, it is possible to detect the distance. The signals of the line array sensors 111L and 111R are introduced into a computer and the distance between the two light beams FL and FR is analyzed and the distances to the eyes EL and ER to be examined are calculated, and a distance adjustment character figure is displayed on the monitor with the image of the anterior eye part, and the examiner adjusts the distance so that the figure may assume a predetermined shape.

During objective refraction measurement, the distant view visual target 105 shown in FIG. 19 is projected onto the left and right eyes EL and ER. The light beam of the light source 127 passes along the optical path 025, and by the selection of the left and right changeover mirror 121, a spot-like light beam is projected from the center of the pupil of one of the left and right eyes EL and ER onto the fundus of the eye. The reflected light thereof returns along the same optical path, passes through the apertured mirror 124 and the pupil periphery six-aperture stop 133, is separated by the light receiving surface of the separating prism 134, passes through the lens 135, is reflected by the dichroic mirror 131 and is received by the image pickup means 132. The positions of these six light beams obtained by the image pickup means are analyzed by a computer to thereby calculate a refractive value.

During near eye examination, the movable lens 102 is retracted from the optical path 021 to a position indicated by dotted line. The visual target 105 moves on the optical path 021 with the illuminating light source 106 and is set at a predetermined eye examination distance, and in conformity therewith, the angles of the mirrors 101L and 101R are adjusted to thereby give an angle conformity to the distance to the optical paths 020L and 020R before the eyes so that the visual target 105 and the visual targets 118L and 118R may assume the same convergence angles. At this time, the visual target 105 is changed from a distant view, to a close-range view or a geometric pattern.

Figure 21:
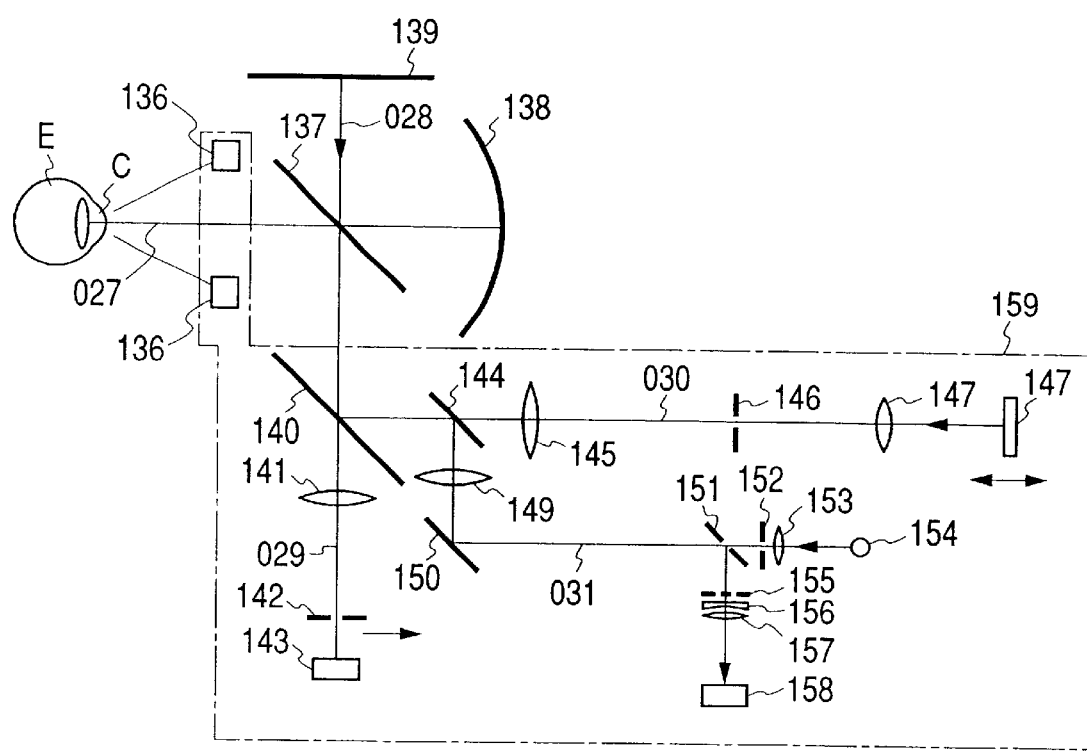
FIG. 21 is a side view of an optical system according to a seventh embodiment.

FIG. 21 is a side view of a seventh embodiment having the compound function of an auto-refractometer and an auto-keratometer, and ring light sources 136 for measuring the curvature of cornea are disposed obliquely forwardly of the eye E to be examined, and on an optical path 027 forward of the eye E to be examined, there are disposed a light dividing member 137 which reflects infrared light and becomes a half mirror for visible light and of which the lateral size is larger than the width between both eyes, and a concave mirror 138 of which the lateral diameter is larger than the width between the eyes. A binocular visual target optical path is provided in the direction of reflection above the light dividing member 137, and there is disposed a visual target 139 on which a distant view similar to that in FIG. 19 is depicted. The visual target 139 is near the focus of the concave mirror 138, and the visual angle thereof is 20° to 30°, and the visual target 139 of a wide field of view having an optical axis parallel to the both eyes is presented, whereby a far seeing feeling is given to the examinee S.

Also, on an optical path 029 in the direction of reflection below the light dividing member 137, there are successively arranged a light dividing member 140, a lens 141, a stop 142 retractably insertable onto the optical path 029, and image pickup means 143 for the observation of the anterior eye part during refraction measurement and cornea measurement. On an optical path 030 in the direction of incidence of the light dividing member 140, there are arranged a light dividing member 144, a lens 145, a stop 146, a lens 147 and a visual target 148, which has a visual angle of the order of 3° to 5° and is the central visual target of the same distant view as the visual target 139 and of which the diopter is variable in conformity with the degree of refraction.

Also, on an optical path 031 in the direction of reflection of the light dividing member 144, there are arranged a lens 149, a mirror 150, an apertured mirror 151, a stop 152, a lens 153 and a light source 154, and in the direction of reflection of the apertured mirror 151, there are arranged a six-aperture stop 155, a separating prism 156, a lens 157 and image pickup means 158. The light dividing member 140 is adapted to reflect visible light and the wavelength light of the light source 154 and transmit the wavelength of the ring light sources 136 therethrough, and the light dividing member 144 is adapted to transmit visible light therethrough and reflect the light from the light source 154. An eye examining optical system 159 encircled by a dotted line is movable as a unit by an average eye width distance in the direction of the width between the eyes relative to the visual target optical system.

By the above-described construction, the examinee S sees the visual target 139 with his both eyes through the light dividing member 137 and the concave mirror 138. Also, the central visual target 148 is overlappingly projected through the lens 147, the stop 146, the lens 145 and the light dividing members 144, 140 and 137.

The left and right eyes are changed over and the measuring optical system is moved to the front of the eye E to be examined, and the anterior eye part is illuminated by the ring light sources 136, and the reflected image thereof by the cornea C is picked up by the image pickup means 143 through the light dividing members 137 and 140, the lens 141 and the stop 142. The image by the image pickup means 143 is displayed on a monitor, not shown, and the examiner sees it and effects alignment.

During cornea measurement, the stop 142 is inserted into the optical path 029, and as described above, the ring image passed through the optical path 029 is picked up by the image pickup means 143, and the position of this image is analyzed by the computer and the curvature of the cornea C is found. The lens 145 images the pupil on the stop 146, and since the stop 146 is at the front side focus position of the lens 147, the visual angle does not change even if the visual target 148 is moved toward the optical path 030 to change the diopter thereof.

The refraction measuring optical system is similar to that in the first embodiment, and the light beam from the light source 154 passes through the lens 153, the stop 152, the apertured mirror 151, the mirror 150, the lens 149 and the light dividing members 144, 140 and 137 and projects a spot light onto the fundus of the eye, and the reflected light from the fundus of the eye returns along the optical paths 027, 029 and 031, and is reflected by the apertured mirror 151, and the spot light separated into six light beams through the six-aperture stop 155, the separating prism 156 and the lens 157 is received by the image pickup means 158, and the position thereof is calculated by the computer and the refractive value is calculated. The image pickup means 158 can be the same as the image pickup means 143.

As described above, the eye examining apparatus according to the present invention starts the driving of the driving means when the examinee's face is detected by the detecting means, whereby alignment can be automatically performed even if the position of the eye to be examined deviates greatly.

Also, the eye examining apparatus according to the present invention adjusts alignment by the alignment means after the distance is adjusted by the distance adjusting means, whereby alignment can be automatically performed even if the position of the eye to be examined deviated greatly.

What is claimed is:

1. An eye examining apparatus comprising:
    a projection optical system for projecting a light beam onto an eye to be examined;
    an eye examining optical system for receiving the light of said projection optical system reflected from the eye to be examined and examining the eye to be examined;
    a face detecting system fro detecting the presence of an examinee's face;
    a driving system for driving said eye examining optical system; and
    a control system for starting driving of said driving system on the basis of the result of the detection by said face detecting system.

2. An eye examining apparatus according to claim 1, wherein said face detecting system has an image pickup member for picking up the image of the anterior eye part of the eye to be examined, and the examinee's face is detected by the image pickup signal of said image pickup member.

3. An eye examining apparatus comprising:
    a projection optical system for projecting a light beam onto an eye to be examined; and
    an eye examining system for receiving the light of said projection optical system reflected from the eye to be examined and examining the eye to be examined;
    said eye examining system having detecting means for detecting distance adjustment and alignment state relative to said eye to be examined, said eye examining system being driven so as to adjust the alignment after the distance adjustment of said eye examining system is performed.

4. An eye examining apparatus comprising:
    a projection optical system for projecting a light beam onto an eye to be examined;
    an eye examining system for receiving the light of said projection optical system reflected from the eye to be examined and examining the eye to be examined;
    a detecting system for detecting the positional state of the eye to be examined;
    face fixing means driven to fixe the eye to be examined; and
    drive controlling means for driving said face fixing means on the basis of the detection signal of said detecting system.

5. An eye examining apparatus comprising:
    a projection optical system for projecting a light beam onto an eye to be examined;
    an eye examining system for receiving the light of said projection optical system reflected from the eye to be examined and examining the eye to be examined;
    an image pickup member for picking up the image of the anterior eye part of the eye to be examined;
    discriminating means for discriminating the state of the eye to be examined on the basis of the signal of said image pickup member; and
    instructing means for giving predetermined instructions to an examinee on the basis of the discrimination signal of said discriminating means.

6. An apparatus according to claim 5, wherein said discriminating means discriminates whether the eyelid is hampering the light beam of said projection optical system or not.

7. An eye examining apparatus comprising:
    a face fixing means for fixing the face with the eye to be examined;
    an eye examining optical system having a detecting means for detecting the eye to be examined, which is movable with respect to said face fixing means;
    a control system for controlling said face fixing means on the basis of the detection of said detecting means.

8. An eye examining apparatus comprising:
    a light projecting mean for projecting light to the eye to be examined;
    an eye examining optical system having an imaging optics for imaging the eye to be examined with two apertures;
    a detecting system for detecting the corneal reflection of the light of said light projecting means in the image of the eye imaged by said imaging optics with the two apertures;
    a driving means for driving said eye examining optical system on the basis of the detection of said detecting system.

9. An eye examining apparatus comprising:
    an examining system having a light source and an optical element for examining an eye with a light beam;
    an image-pickup device which takes images of an anterior part of the eye including a pupil of the eye;
    a detecting system for detecting a lowered state of an eyelid of the eye by using signals of said image-pickup device; and
    an indicator that indicates a warning when the eyelid lowers to cover a part of the pupil so that it hampers the light beam, based on the detection of said detecting system.

10. An apparatus according to claim 9, further comprising a visual target system which provides a visual target for the examinee to view.

11. An apparatus according to claim 10, further comprising an actuator to move said examining system relative to the eye for alignment.

12. An eye examining apparatus comprising:
    an eye examining system for examining an eye by detecting the light reflected from the eye of light projected to the eye;
    a chin rest which is vertically adjustable;
    a spring for moving said chin rest upward; and
    a stopper for stopping the movement of said chin rest.

* * * * *

UNITED STATES PATENT AND TRADEMARK OFFICE
CERTIFICATE OF CORRECTION

PATENT NO. : 6,309,068 B1
DATED : October 30, 2001
INVENTOR(S) : Yoshimi Kohayakawa It is certified that error appears in the above-identified patent and that said Letters Patent is hereby corrected as shown below:

Column 9,
Line 11, "Judged" should read -- judged --.
Line 62, "dioper" should read -- diopter --.

Column 15,
Line 29, "fro" should read -- for --.
Line 61, "fixe" should read -- fix --.

Column 16,
Line 28, "mean" should read -- means --.

Signed and Sealed this

Twenty-third Day of July, 2002

*Attest:*

*Attesting Officer*

JAMES E. ROGAN
*Director of the United States Patent and Trademark Office*